(12) United States Patent
Byers

(10) Patent No.: US 8,434,636 B2
(45) Date of Patent: May 7, 2013

(54) CULTURING CONTAINER WITH FILTER VENTS

(75) Inventor: Ronald E. Byers, Longmont, CO (US)

(73) Assignee: Byers Industries, Inc., Longmont, CO (US)

( * ) Notice: Subject to any disclaimer, the term of this patent is extended or adjusted under 35 U.S.C. 154(b) by 199 days.

(21) Appl. No.: 12/927,666

(22) Filed: Nov. 22, 2010

(65) Prior Publication Data

US 2012/0125936 A1    May 24, 2012

(51) Int. Cl.
*B65D 51/00* (2006.01)
*B65D 51/16* (2006.01)
*B65D 21/00* (2006.01)
*B65D 85/62* (2006.01)

(52) U.S. Cl.
USPC ......... 220/367.1; 220/200; 220/371; 215/308

(58) Field of Classification Search .................. 220/200, 220/367.1, 371; 215/308; 206/508
See application file for complete search history.

(56) References Cited

U.S. PATENT DOCUMENTS

| | | | |
|---|---|---|---|
| 3,055,808 | A | 9/1962 | Henderson |
| 6,426,046 | B1 | 7/2002 | Cassells et al. |
| 6,913,152 | B2 | 7/2005 | Zuk, Jr. |
| 7,172,740 | B2 * | 2/2007 | Gleichauf et al. ............ 422/300 |
| 7,456,925 | B2 | 11/2008 | Kim |
| 2002/0096468 | A1 | 7/2002 | Zuk |
| 2003/0052125 | A1 * | 3/2003 | Hayes et al. ................. 220/4.23 |
| 2009/0321462 | A1 * | 12/2009 | Hui ............................. 220/780 |
| 2010/0015694 | A1 | 1/2010 | Acosta |

* cited by examiner

*Primary Examiner* — Anthony Stashick
*Assistant Examiner* — Madison L Poos
(74) *Attorney, Agent, or Firm* — Harold A. Burdick

(57) ABSTRACT

A culturing container is disclosed having a container base and a container cover with plural vent openings. Plural filter retaining frames are affixed surrounding the vent openings to accommodate filter retention across the vent openings thereby establishing plural integral filter vents in the container cover. Multi-ridge outer peripheries of the container base and the container cover are engageable to provide substantially air-tight container sealing.

20 Claims, 5 Drawing Sheets

CULTURING CONTAINER WITH FILTER VENTS

FIELD OF THE INVENTION

This invention relates to culture cups and dishes, and, more particularly, relates to vented culturing containers.

BACKGROUND OF THE INVENTION

Laboratory and research facility utilities for growing, or culturing, living material in a prepared nutrient medium are known. Petri dishes, culture cups and the like used for such purposes have heretofore included various structural adaptation and/or supplemental means to seal the material and medium in the apparatus sheltered from the ambient (see, for example, U.S. Pat. No. 3,055,808).

Various filtering arrangements used in association with sample dishes (see, for example, U.S. Patent Application Publication No. 2010/0015694) and liquid sample filtration cups (see U.S. Patent Application Publication No. 2002/0096468 and U.S. Pat. Nos. 6,913,152 and 7,546,925, for example) have also been heretofore suggested and/or utilized for various purposes. Often such heretofore known devices are unduly complex, are difficult to store when not in use and maintain when in use, and/or provide inadequate sealing and air circulation for culture growth. Further improvement could thus still be utilized.

SUMMARY OF THE INVENTION

A sealable culturing container, such as a culture cup or the like, having improved container sealing and filter vent structure is provided by this invention. The container is structurally simple and easy to use, store and maintain, and provides efficient sealing of medium/samples from the ambient while still providing sufficient filtered air circulation for culture growth.

The container accommodates growth of plants or samples that need air while maintaining a contaminant free growth environment. The container is preferably sealed by a multi-point seal interface to prevent contamination from the ambient, a filter or filters held and sealed at the container, preferably by ultrasonic welding. The container preferably includes structure making container stacking easy without blocking air flow through the filters of each container in a stack.

The culturing container of this invention includes a container base having an open aspect. A container cover with plural vent openings therein is releasably securable over the open aspect of the container base. Plural media (filter or rubber media, for example) retaining frames are affixed surrounding the vent openings to accommodate media retention across the vent openings.

The frames, vent openings and filter media retained thereacross together establish plural integral filter vents in the container cover when the frames are sealingly adapted around a margin of the openings. The container is sealable by provision of a multi-ridge outer periphery adjacent to the open aspect of the container base, an inter-ridge groove established by the multi-ridge outer periphery of the base. The container cover also includes multi-ridge outer periphery with an inter-ridge groove established thereat for substantially air-tight engagement with the multi-ridge outer periphery of the base.

It is therefore an object of this invention to provide an improved sealable culturing container.

It is another object of this invention to provide a sealable culturing container with filter vents.

It is still another object of this invention to provide a culturing container with plural filtered vents.

It is yet another object of this invention to provide a culturing container that is structurally simple and easy to use, store and maintain.

It is still another object of this invention to provide a culturing container that accommodates efficient sealing of medium/samples from the ambient while still providing sufficient air circulation for culture growth.

It is another object of this invention to provide a culturing container having a container base with an open aspect, a container cover with plural vent openings therein, the cover releasably securable over the open aspect of the container base, and plural media retaining frames each one of which is affixed surrounding a different one of the vent openings to thereby accommodate media retention across the vent openings.

It is still another object of this invention to provide a culturing container having a container base with an open aspect, and a container cover having plural integral filter vents therein, each of the filter vents defined by a cover opening having filter media retained thereacross by a frame sealingly adapted around a margin of the opening.

It is yet another object of this invention to provide a sealable culturing container that includes a container base having an open aspect, the container base including a multi-ridge outer periphery adjacent to the open aspect with an inter-ridge groove established thereby, a container cover configured for releasable securement over the open aspect of the container base and having a multi-ridge outer periphery with an inter-ridge groove established thereby for substantially air-tight engagement with the multi-ridge outer periphery of the base, and filter vent structure established at the container.

With these and other objects in view, which will become apparent to one skilled in the art as the description proceeds, this invention resides in the novel construction, combination, and arrangement of parts substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which.

DESCRIPTION OF THE INVENTION

Figure 1:
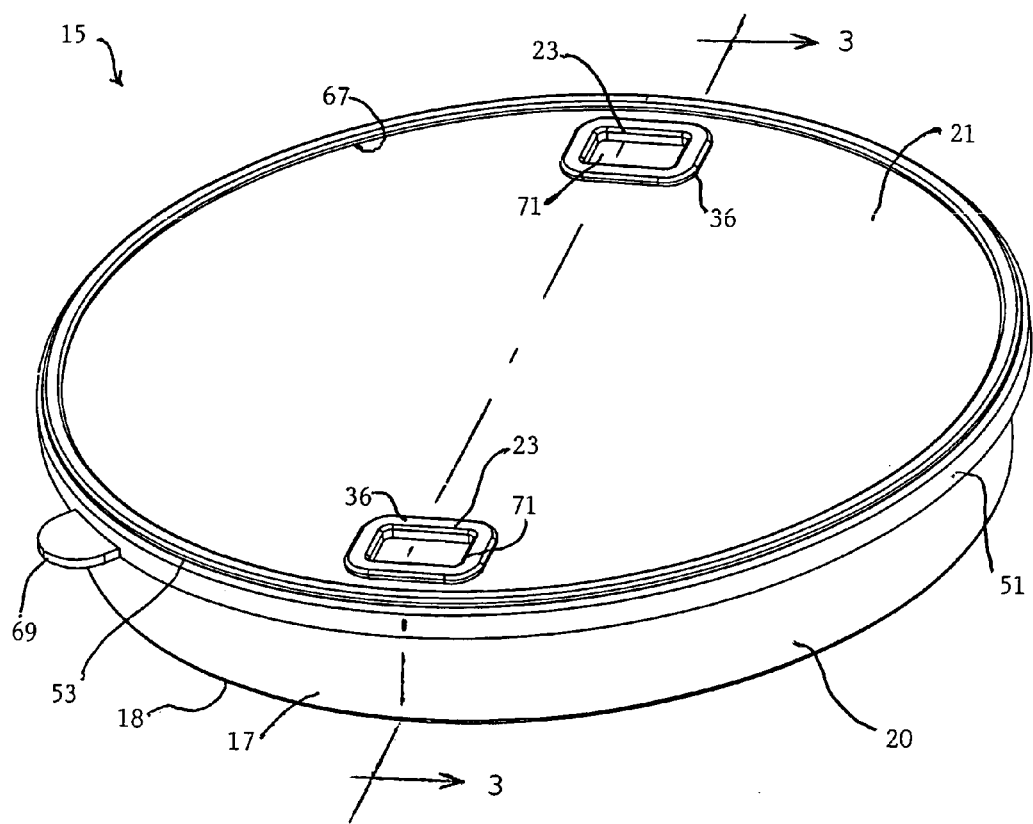
FIG. 1 is a perspective view of the culturing container of this invention.
Figure 2:
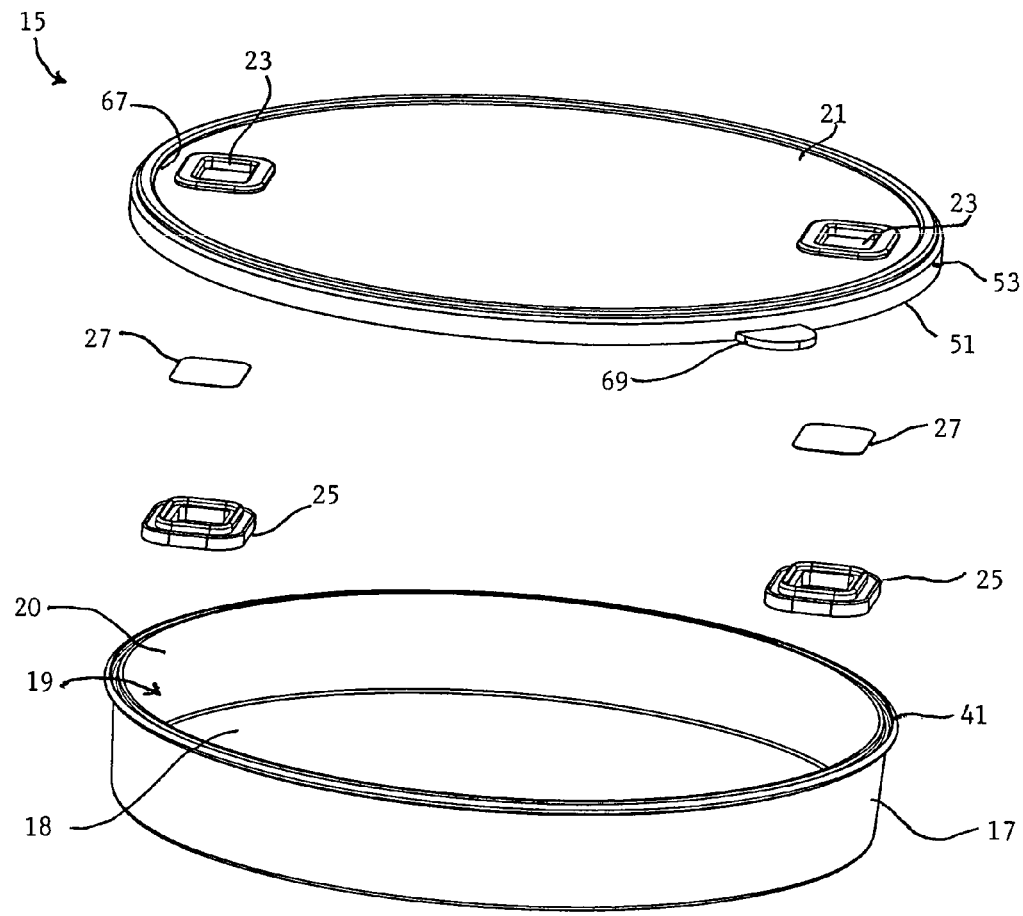
FIG. 2 is an exploded view of the culturing container of FIG. 1.
Figure 3:
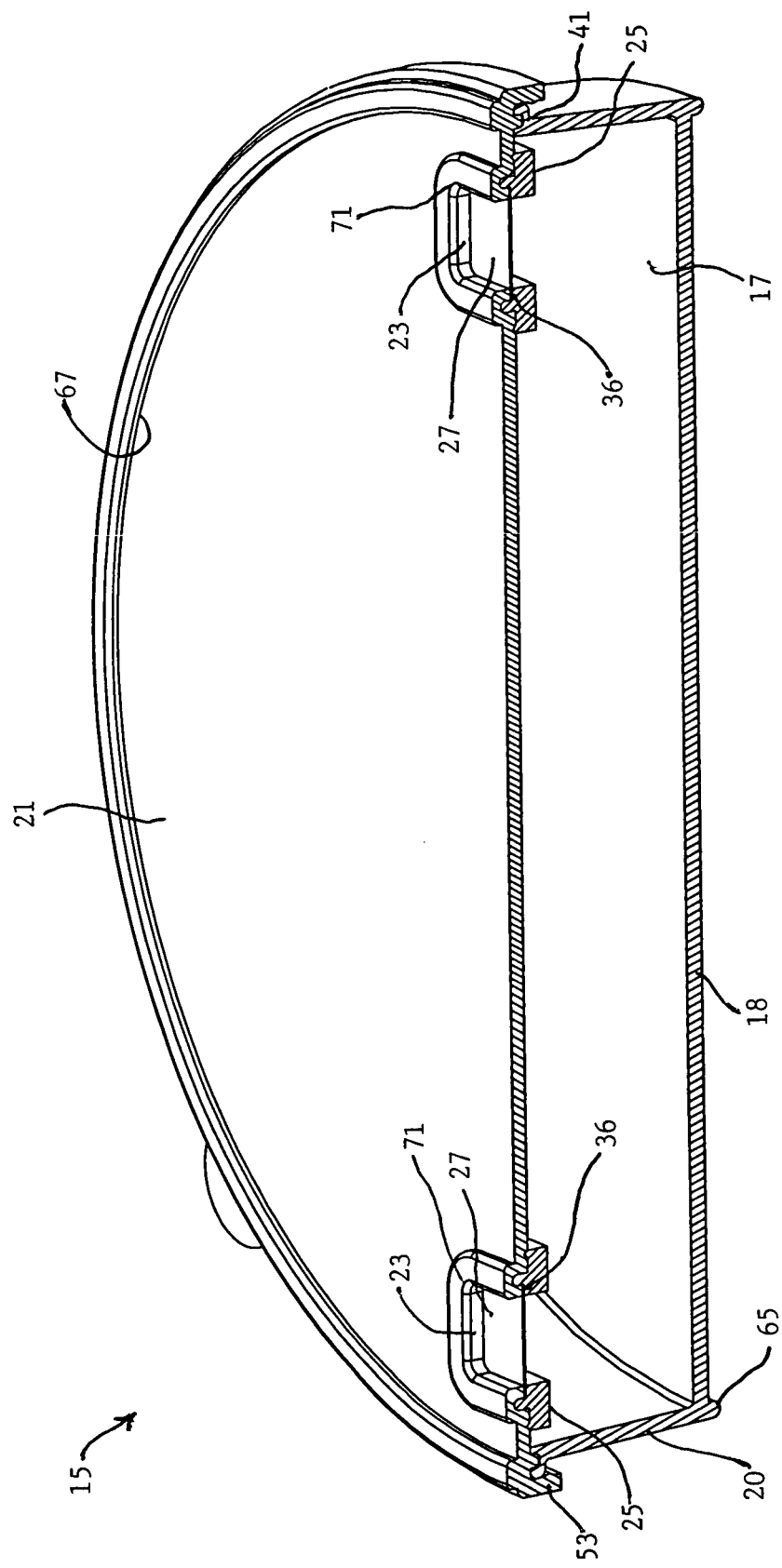
FIG. 3 is a sectional view taken through section lines 3-3 of FIG. 1.

As illustrated in FIGS. 1 through 3, culturing container 15 of this invention includes container base 17 having a bottom surface 18 opposite open aspect 19 defined by annular wall 20 thereby establishing a container volume. Container cover 21 has with plural vent openings 23 therein, the cover releasably securable over the open aspect of the container base. Plural media retaining frames 25 are each affixed surrounding a different one of vent openings to thereby accommodate media 27 retention across the vent openings. Media 27 may be either filter media or self-resealing rubber media depending on the particular use of the vent formed thereby.

Figure 4:
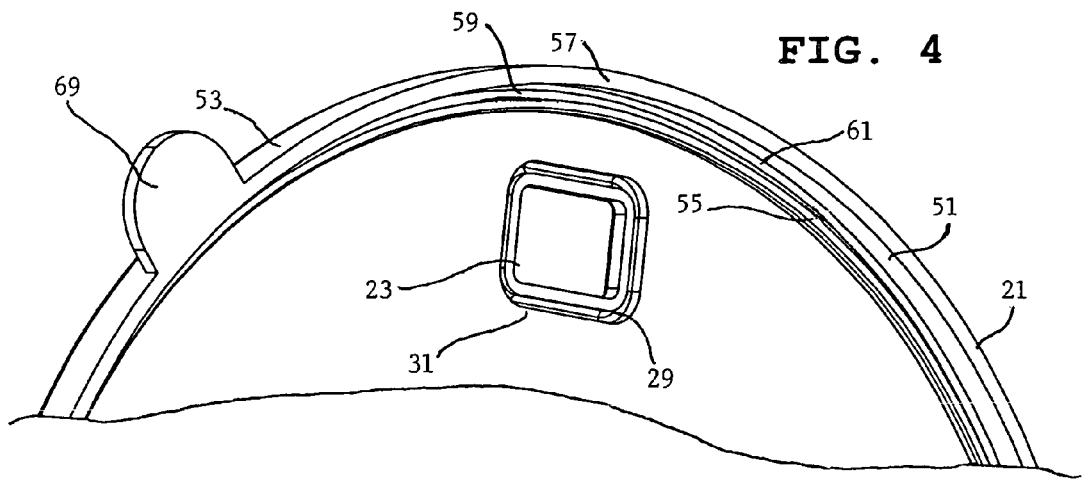
FIG. 4 is a partial perspective view of the inwardly facing side of the cover of the culturing container of this invention.
Figure 5:
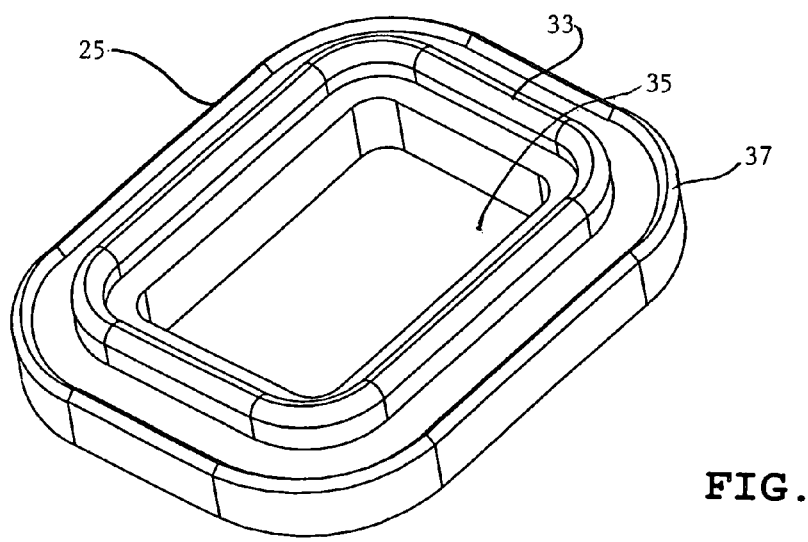
FIG. 5 is a perspective view of a filter retention insert used in the culturing container of this invention.
Figure 6:
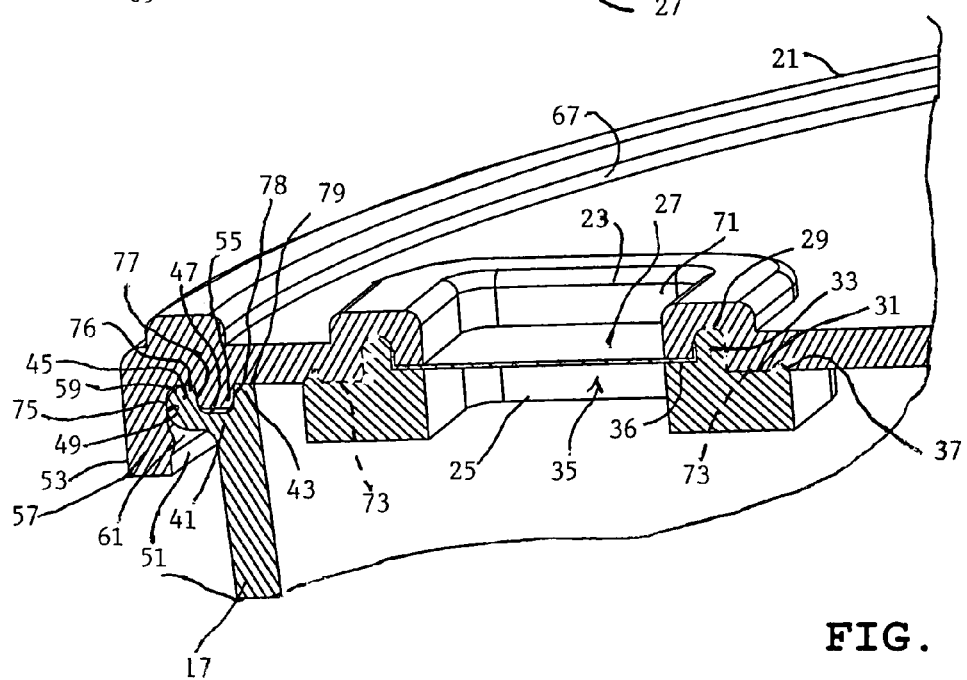
FIG. 6 is a partial sectional perspective view of the assembled culturing container of this invention.

As shown in FIG. 4 through 6, cover 21 has endless grooves 29 formed at the inner surface thereof, each surrounding one of the vent openings 23 at a margin 31 thereof (FIG. 4). Retaining frames 25 each have an endless ridge 33 adjacent to filter vent opening 35 configured for receipt in one of the endless grooves 29 (see FIGS. 5 and 6). The grooves 29, ridges 33 and adjacent structures define components of filter retention interface 36 with filter media 27 sandwiched between the components. Retaining frames 25 further include endless spiked energy directors 37 surrounding ridges 33 accommodating ultrasonic welding (see FIG. 5).

FIG. 6 also illustrates the improved container sealing of this invention. Container base 17 includes a multi-ridge outer periphery 41 adjacent to the open aspect 19 of base 17. Inner and outer annular ridges 43 and 45, respectively, define inter-ridge groove 47 therebetween. Outer annular ridge 45 has a cross-section characterized by arcuate outwardly facing surface 49. Container cover 21 includes multi-ridge outer periphery 51 defined at a distal end of annular rim 53, with inner and outer ridges 55 and 57 defining inter-ridge groove 59 (see also FIG. 4). As shown, ridges 55/57 and groove 59 engage multi-ridge outer periphery 41 of base 17 thereby increasing sealing surface contact between the base and the cover when the cover is secured over the open aspect of the base.

In particular, inter-ridge groove 47 at outer periphery 41 of container base 17 receives ridge 55 of multi-ridge outer periphery 51 of cover 21, and groove 59 of cover 21 receives ridge 45 of multi-ridge outer periphery 41 of base 17. Inwardly facing endless lip 61 established at rim 53 at the end of ridge 57 and adjacent to inter-ridge groove 59 of cover outer periphery 51 traps outer annular ridge 45 as it is moved by a user into inter-ridge groove 59. Rim/ridge 53/57 yields to allow passage of arcuate surface 49 of ridge 45 by lip 61 and thereafter resiliently returns to its original relative position.

Container base 17 is preferably provided with annular stacking ridge 65 receivable in annular stacking interface 67 at the top of cover 21 (see FIG. 3). Ridge 65 is formed by a plurality of intermittent ridge portions (not shown) thus allowing airflow to the vents in cover 21 when containers are stacked. Cover 21 is preferably provided with cover manipulating tab 69 at outer rim 53 (see FIG. 4).

As may be appreciated from the foregoing, filter vents 71 are established in cover 21 by openings 23 having filter media 27 retained thereacross by frames 25 sealingly adapted around margins 31 of openings 23. Vents 71 are preferably integral vent structures formed using known bonding techniques such as ultrasonic welding. In such case, endless spiked energy directors 37 of frames 25 surround filter media 27 to direct ultrasonic energy during the welding process, cover 21 and each frame 25 together forming sealing interface 73 adjacent to the filter retention interface 36 (see FIG. 6). In use, when cover 21 is snapped into position on base 17 across open aspect 19 thereof, multi-ridge outer peripheries 41 and 51 of base 17 and container cover 21, respectively, establish a substantially air-tight engagement having five positive seal points 75, 76, 77, 78 and 79 (see FIG. 6).

Figure 7:
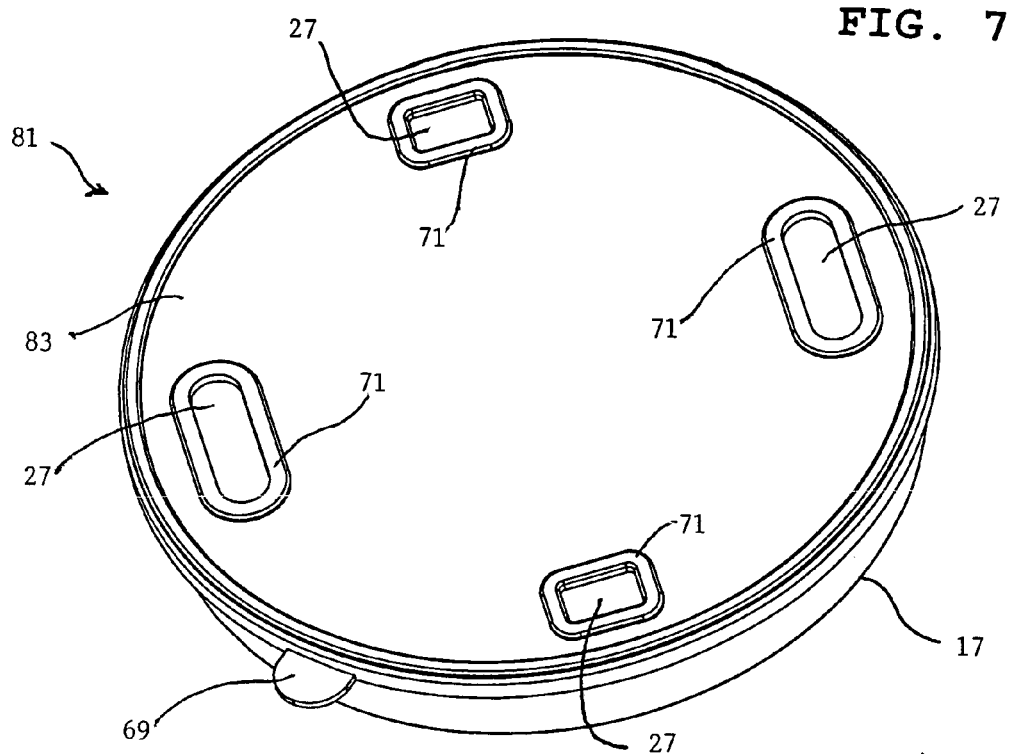
FIG. 7 is a perspective view of an alternative embodiment of the culturing container of this invention illustrating different shapes and/or numbers of filter vents associated therewith.

An alternative embodiment 81 of the culturing container of this invention is shown in FIG. 7. The embodiment shown is for purposes of illustration only (any one or all of the modifications illustrated may be present in any given production piece). Unchanged components retain their identifying numbers in FIG. 7. Cover 83 includes plural filter vents 71 differing in total number (four instead of two, though more or fewer could be provided) and configuration (oval and/or rectangular, though any other shapes could also be utilized). It is intended that different vent sizes, shapes, numbers and positions in the cover may be utilized with this invention as overall usage and manufacturing may dictate.

While the container is illustrated as a cylindrical structure, any other container shape could be utilized. Additionally, while the filter vents are shown preferably incorporated into the container cover, the vents could be established in the container base and/or both the base and the cover.

The vents of this invention may incorporate nearly any relatively flexible filter media that can stand up to ultrasonic welding. Preferred filters will have pore sizes between 0.2 microns and 5 microns depending on intended use. Additional or ancillary vents 71 can be utilized for extraction of cultivated samples by replacing filter media 27 with self-resealing thermoplastic rubber known for such usage.

Base 17, cover 21/83 and frames 25 are all preferably formed using standard plastic injection molding techniques. Cover 21/83, filter media 27 and frames 25 are then assembled (ultrasonically welded, for example, though other bonding techniques can be utilized). After assembly, the base and cover are sterilized (using ethylene oxide, gamma irradiation, or the like) and packaged for distribution. Base 17, cover 21 and frames 25 are preferably made from polycarbonate (thus allowing the product to be autoclaved then reused) or polystyrene resin (and thus disposable). Preferred filter 27 are preferably made of polysulfone or polycarbonate filter media.

What is claimed is:

1. A culturing container comprising:
   a container base having an open aspect and a multi-ridge outer periphery adjacent to said open aspect;
   a container cover with plural vent openings therein and having a multi-ridge outer periphery for substantially air-tight engagement with said multi-ridge outer periphery of said base, said cover further including an annular rim having said outer periphery of said cover defined at a distal end thereof, an inwardly facing endless lip established at said rim adjacent to said outer periphery of said cover; and
   plural media retaining frames each one of which is affixed surrounding a different one of said vent openings to thereby accommodate media retention across said vent openings.

2. The container of claim 1 wherein said cover has endless grooves defined therein each surrounding one of said vent openings at a margin thereof, and wherein said retaining frames each have an endless ridge configured for receipt in one of said endless grooves.

3. The container of claim 2 wherein each of said retaining frames includes an endless spiked energy director surrounding said ridge.

4. The container of claim 1 wherein said multi-ridge outer periphery of said container base and said multi-ridge outer periphery of said container cover are configured for increasing sealing surface contact between said base and said cover when said cover is secured over said open aspect of said base.

5. The container of claim 1 wherein said multi-ridge outer periphery of said container base includes an inter-ridge groove for receiving a ridge of said multi-ridge outer periphery of said cover, and wherein said container cover includes an inter-ridge groove at said outer periphery thereof for receiving a ridge of said multi-ridge outer periphery of said base.

6. The container of claim 1 wherein said container base has a bottom surface opposite said open aspect, said bottom surface having a stacking ridge defined thereat.

7. The container of claim 1 wherein said container cover includes a manipulating tab extending therefrom.

8. A culturing container comprising:
   a container base having an open aspect and a multi-ridge outer periphery adjacent to said open aspect; and
   a container cover having plural integral filter vents therein and a multi-ridge outer periphery including an inter-ridge groove for substantially air-tight engagement with said multi-ridge outer periphery of said base, wherein said cover further includes an annular rim having said cover outer periphery defined at a distal end thereof, an inwardly facing endless lip established at said rim adjacent to said inter-ridge groove of said cover outer periphery, each of said filter vents defined by a cover opening having filter media retained thereacross by a frame sealingly adapted around a margin of said opening.

9. The container of claim 8 wherein said integral filter vents are integrated by ultrasonic welding.

10. The container of claim 9 wherein each said frame includes an endless spiked energy director therearound.

11. The container of claim 10 wherein said filter media is surrounded by said endless spiked energy director.

12. The container of claim 8 wherein said cover and each said frame include components of a filter retention interface.

13. The container of claim 12 wherein said filter media is sandwiched between said components of said retention interface.

14. The container of claim 12 wherein said cover and each said frame include a sealing interface adjacent to said filter retention interface.

15. A sealable culturing container comprising:
   a container base having an open aspect, said container base including a multi-ridge outer periphery adjacent to said open aspect with an inter-ridge groove established thereby;
   a container cover configured for releasable securement over said open aspect of said container base and having a multi-ridge outer periphery with an inter-ridge groove established thereby for substantially air-tight engagement with said multi-ridge outer periphery of said base, said cover including an annular rim having said cover outer periphery defined at a distal end thereof, an inwardly facing endless lip established at said rim adjacent to said inter-ridge groove of said cover outer periphery; and
   filter vent structure established at said container.

16. The container of claim 15 wherein said filter vent structure includes first and second filter vents each including a filter retention interface.

17. The container of claim 16 further comprising filter media at each said filter retention interface.

18. The container of claim 15 wherein said filter vent structure includes a filter vent opening and a filter retaining frame affixable around said opening.

19. The container of claim 15 wherein said container base has a bottom opposite said open aspect, said bottom including an adaptation accommodating container stacking defined thereat.

20. The container of claim 15 wherein said multi-ridge outer periphery of said container base includes an outer annular ridge with a cross-section characterized by an arcuate outwardly facing surface, said outer annular ridge receivable in said inter-ridge groove of said cover outer periphery with said rim yielding to allowing passage of said arcuate surface of said outer annular ridge by said lip of said rim.

\* \* \* \* \*